(12) United States Patent
Meyer et al.

(10) Patent No.: US 6,329,352 B1
(45) Date of Patent: Dec. 11, 2001

(54) METHOD AND COMPOSITION FOR TREATING SLEEP APNEA

(75) Inventors: Keith C. Meyer, Middleton, WI (US); M. Safwan Badr, West Bloomfield, MI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/313,110

(22) Filed: May 17, 1999

Related U.S. Application Data

(63) Continuation of application No. 08/834,369, filed on Apr. 16, 1997, now Pat. No. 5,958,902.

(51) Int. Cl.[7] ................................................. A61K 31/685
(52) U.S. Cl. ............................................... 514/76; 514/77
(58) Field of Search ........................................ 514/76, 77

(56) References Cited

U.S. PATENT DOCUMENTS

| | | | |
|---|---|---|---|
| 4,826,821 | 5/1989 | Clements | 514/128 |
| 5,238,920 | 8/1993 | Sarin et al. | 514/12 |
| 5,302,581 | 4/1994 | Sarin et al. | 514/12 |
| 5,547,937 | 8/1996 | Dhaon et al. | 514/12 |
| 5,569,679 | 10/1996 | Jacob | 514/711 |

FOREIGN PATENT DOCUMENTS

| | | | |
|---|---|---|---|
| 2022443 | 2/1991 | (CA) | 15/8 |
| 2042635 | 11/1991 | (CA) | 15/8 |
| WO 87/06943 | 11/1987 | (WO) | 15/6 |
| WO 93/21221 | 10/1993 | (WO) | 7/8 |

OTHER PUBLICATIONS

Lewis and Jobe, Surfactant and the Adult Respiratory Distress Syndrome, Am. Rev. Respir. Dis., vol. 147, pp. 218–233, 1993. published sufficiently before filing date that the month is not in issue.

Girod et al., Phosphlipid Composition and Surface—Active Properties of Trachcobronchial Secretions from Patients with Cystic Fibrosis and Chronic Obstructive Pulmonary Disease, Pediatric Pulmonology vol. 13, pp. 22–27 (1992). published sufficiently before filing date that the month is not in issue.

Witek and Schachter, Pharmacology and Therapeutics in Respiratory Care, W.B. Saunders Co., pp. 334–336, 1994. published sufficiently before filing date that the month is not in issue.

Merrit and Halliday, On Exogenous Surfactant Therapy, Pediatric Pulmonology, vol. 14 pp. 1–3, 1992. published sufficiently before filing date that the month is not in issue.

Miki et al., Effects of Pharyngeal Lubrication on the Opening of Obstructed Upper Airway, J. Applied Phys., vol. 72, pp. 2311–2316, 1992. published sufficiently before filing date that the month is not in issue.

T. Van der Touw, The Role of Synthetic Surfactant in Promoting Upper Airway Patency During Negative Airway Pressure in Awake Subjects, Am. J. Respir. Crit. Care Med, vol. 149, p. A865, 1994. published sufficiently before filing date that the month is not in issue.

Widdicombe and Davies, The Effects of a Mixture of Surface–active Agents (Sonarex) on Upper Airways Resistance and Snoring in Anaesthetized Dogs, Eur. Respir. J., vol. 1, pp. 785–791, 1988. published sufficiently before filing date that the month is not in issue.

Hoffstein et al., Reduction in Snoring with Phosphocholinamin, a Long–acting Tissue–lubricating Agent, Am. J. Otolaryngol, vol. 8, pp. 236–240, 1987. published sufficiently before filing date that the month is not in issue.

Biosis Abstract 77:189178 (1976) Koch.

Chemical Abstracts 111:127039 (1987) Hibino et al.

Hida, Watura, "Factors Affecting Upper Airway Patency," Japanese Journal of Thoracic Diseases, 28:1, pp. 22–28, Jan. 1990 (as translated).

*Primary Examiner*—Zohreh Fay
(74) *Attorney, Agent, or Firm*—Michael Best & Friedrich LLP; Grady J. Frenchick

(57) ABSTRACT

Application of synthetic or naturally occurring lung surfactant to the posterior pharyngeal region prior to a period of sleep significantly reduces episodes of sleep disturbance resulting in apnea or hypopnea. The present invention provides lung surfactant in a convenient applicator container for easy use and storage. Incidents of oxygen desaturation are reduced, thereby lowering the risks of apnea-associated pathologies.

14 Claims, 1 Drawing Sheet

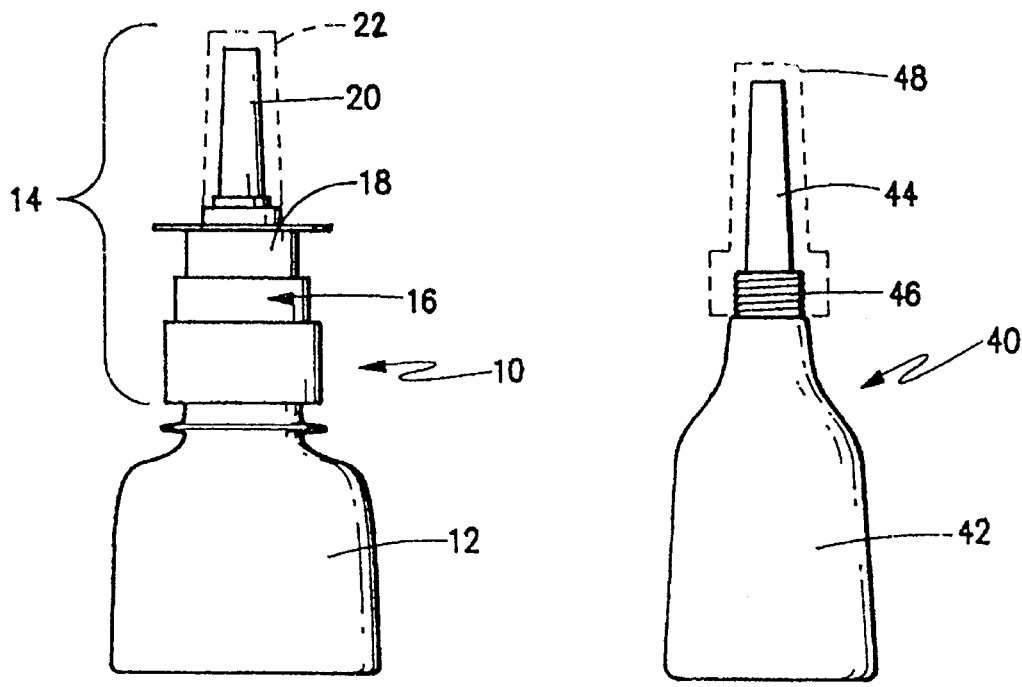
Fig.1
(PRIOR ART)
Fig.2
(PRIOR ART)
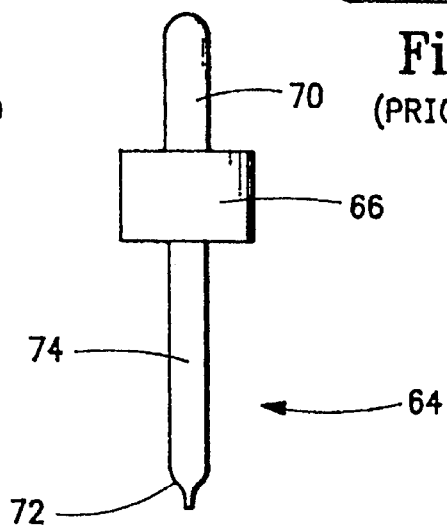
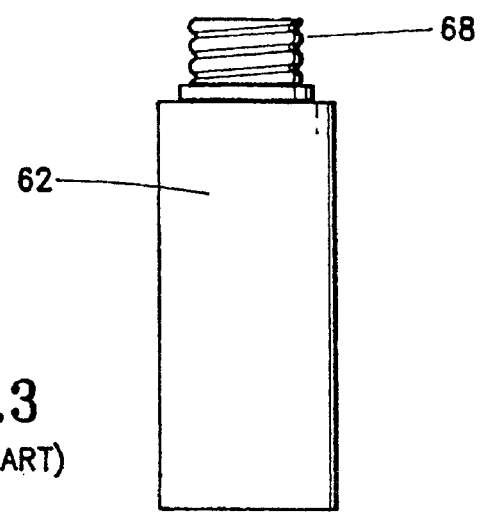
Fig.3
(PRIOR ART)

METHOD AND COMPOSITION FOR TREATING SLEEP APNEA

CROSS-REFERENCE TO RELATED APPLICATION

This application is a continuation of U.S. patent application Ser. No. 08/834,369, filed Apr. 16, 1997, now U.S. Pat. No. 5,958,902.

STATEMENT REGARDING FEDERALLY SPONSORED RESEARCH OR DEVELOPMENT

This invention was made with United States government support awarded by the following Agencies:
NIH HL02588 and HL53443
The United States has certain rights in this invention.

FIELD OF THE INVENTION

The present invention relates to a treatment for sleep apnea using natural or synthetic lung surfactant to coat the pharyngeal mucosa. The invention thereby provides therapeutic relief for a medical condition having serious adverse health effects. An apparatus is also provided for therapeutic administration of the surfactant.

BACKGROUND OF THE INVENTION

Among the most troublesome of sleep impairing ailments is persistent snoring and associated sleep apnea during which normal breathing is interrupted for a sufficient time to produce anoxia. Episodes of apnea occur with sufficient frequency that the subject is deprived of the normal benefits of restful sleep, and frequently suffers from profound daytime drowsiness, mental fatigue, and weakness. Snoring occurs in the collapsible part of the airway from the epiglottis to the choanae involving the soft palate, uvula, tonsils, tonsillar pillars, and the pharyngeal muscles and mucosa. In apnea, the air passage becomes completely occluded, interrupting breathing. Typically periods of loud snoring are punctuated with silent episodes in which the airway is occluded, followed by a loud resuscitative snort which restores breathing and partially wakes the sleeper.

Mild cases of snoring and apnea are nuisances easily tolerated, but more severe cases entail health risks that are only beginning to be studied and understood. A pathological condition exists when apnea episodes extend longer than 10 seconds and occur more than 7–10 times in an hour. When airflow is reduced to 30% of normal, hypopnea or a hypopneic episode ensues. The number of apneas and hypopneas together are taken into account when assessing the severity of the problem. The sum of apneas and hypopneas occurring in an hour is termed the apnea-hypopnea index or the respiratory disturbance index.

Sleep apnea has been associated with arterial hypertension, electrocardiographic changes and arrhythmias, and even sudden death. For a general review of the pathologies associated with sleep apnea by statistical evaluation, see *Sleep and Breathing*, ed. N. A. Saunders, 2 ed., Marcel Dekker, N.Y.: 1994. There are other correlations between brain asthma, brain infarction, and other neurological pathologies. In one Finnish study, 68% of stroke victims studied had a history of severe snoring and sleep apnea. There is a further correlation between habitual sleep apnea and arterial hypertension, another condition associated with stroke prevalence.

Cahan, et al., Chest, 1990; 98: 122s reported a significant correlation between a moderate apnea-hypopnea index (>15) and elevation in insulin levels. At index values greater than 40, fasting hyperglycemia and hyperinsulinemia were observed. Cushing's disease and acromegaly are two further diseases associated with both sleep apnea and insulin resistance, as described in Fairbanks, et al., *Snoring and Obstructive Sleep Apnea*, 2ed., Raven Press, Ltd., New York: 1994.

There have been many modes of treatment proposed for snoring and sleep apnea. Over three hundred devices and treatment methods have received patents in the U.S. Patent and Trademark Office. These include body appurtenances as disclosed, for example, in U.S. Pat. No. 1,216,679 (a snore ball designed to discourage sleeping on the back), U.S. Pat. No. 2,339,998 (a chin strap), U.S. Pat. No. 3,696,377 (a snore activated microphone), U.S. Pat. No. 3,998,209 (a snore trainer delivering an electric shock), U.S. Pat. No. 5,284,829 (a mouth held appliance), and U.S. Pat. No. 5,154,184 (adjustable snore device). One device of interest is a tongue-retaining device, which pulls the superior aspect of the tongue forward, thereby keeping the tongue away from the posterior wall of the pharynx. Most of these devices have limited value, as they only superficially address the actual anatomical bases of snoring and windpath occlusion, or create uncomfortable wearing conditions worse than the snoring and apnea.

The most successful treatment device has been the use of continuous positive airway pressure, as described in Sanders, et al., Chest, 1984; 86: 839. However, very few patients are tolerant of the device, because of the continuous presence of tubes within the mouth and pharyngeal passages. As a last resort, this approach has proven efficacious for some patients, but is often poorly tolerated and compliance may be difficult.

Surgical intervention has been utilized extensively, either by bypassing the obstructive area by tracheostomy or eliminating the obstruction by excision. The latter excision can involve removal of excessive oropharyngeal issues such as an edematous uvula, redundant mucosal folds of the pharyngeal wall, excessive tissue in the soft palate, overly large tonsils, and redundant pillar mucosa. Depending on the particular structures implicated in the airway obstruction, many surgical strategies have been developed. For a general description of such strategies, see Fujita, "Pharyngeal Surgery for Obstructive Sleep Apnea and Snoring," in *Snoring and Obstructive Sleep Apnea*, 2ed., supra. The drawbacks to surgical intervention include the usual risks of invasive procedures in addition to creating problems with swallowing, speaking, and other daytime activities without relieving the snoring and apnea. The observed anatomical defects usually do not deviate much from normal, so that the benefits of surgery are often insignificant.

Good medical practice also recommends reducing known risk factors for sleep apnea, which are sometimes completely effective for diminishing the problem to tolerable levels. These include eliminating obesity (Smith, et al., *Ann. Int. Med.*, 1985, 102: 850), curtailing alcohol consumption (Issa, et al., *J. Neurol. Neurosurg. Psychiatry* 1982, 45: 353.), avoiding certain drugs known to exacerbate the problem such as flurazepam and other benzodiazepines, and manipulating sleep position. The use of many devices noted above reflects an attempt to constrain the body in a posture which reduces or eliminates snoring and sleep apnea.

Finally, there have been efforts to reduce or eliminate snoring and sleep apnea by the administration of therapeutic agents. In several studies protriptyline, a nonsedating, tricyclic antidepressant was administered. Although some reduction in apnea episodes was noted, there was a corresponding increase in hypopneas corresponding to the shorting of REM sleep associated with apnea. In addition, side effects are observed including urinary hesitancy, impotence, rash, and ataxia. Medroxyprotesterone acetate has also been used, but without statistically significant benefit. Similarly, administration of tryptophan, a serotonin precursor, has shown little efficacy.

Some reduction in snoring utilizing phophocholinamin as a topical lubricant was noted in human subjects, as described in *Am. J. Otolaarygol.*, 8: 236 (1987). U.S. Pat. No. 5,569,679 discloses topical use of methylsulfonylethane applied to nasal passages from a dispenser to relieve snoring. Widdlcombe, et al. *Eur. Respir. J.*, 1:785 (1988) reported that Sonarex®, a commercial preparation of surface active agents, reduced the sound of snoring and decreased upper airway resistance in dogs. However, to date no effective drug therapy specifically for sleep apnea has been demonstrated in humans.

SUMMARY OF THE INVENTION

The relation between snoring and sleep apnea is associational but not necessarily causative. Therefore, therapies focussing on reduction in snoring may not decrease by as significant an extent episodes of hypopnea and apnea. Snoring per se, while bothersome to the sleeper and annoying to companions, is not necessarily pathological or seriously harmful. It is therefore an object of the present invention to develop a therapy for sleep apnea and hypopnea leading to significant reduction in such episodes, whether or not there is a concomitant reduction in snoring. Another object is to provide a convenient method and apparatus of using the therapy which is not invasive or distracting, or which produces serious discomfort. A still further object is to provide an effective therapy for alleviating sleep hypopnea and apnea episodes in a single pre-sleep treatment without disturbing the sleeper during a normal 7–9 hour period of rest.

In accordance with the present invention, a pulmonary alveolar surfactant preparation in a physiologically compatible liquid vehicle is applied to the posterior pharyngeal region of a patient in a pharmacologically effective dose prior to a period of sleep. Such pharmacologically effective dose may range from 0.25 to 2.75 mg, generally administered in 0.75 to 1.25 ml, a volume sufficient to coat the affected region without excessive draining to the throat. The method further provides for such application of a surfactant substance containing phospholipid-containing ingredients capable of lowering the surface tension of water to about 15–50 $nM^{*-1}$. The surfactant preparation of the present method may optionally include apoproteins selected from SP-A, SP-B, SP-C, and SP-D in a pharmacologically effective dose, and further optionally, neutral lipids. A pharmacologically effective dose of the apoproteins will be a level from 10 ug to 150 ug, but functionally in a range to achieve anchoring of the phospholipid moieties contained in the surfactant to the pharyngeal tissue. The phospholipids are typically selected from saturated phosphatidylcholine, unsaturated phosphatidylcholine, phosphatidylglycerol, dipalmitoylphosphatidylcholine, and combinations.

In the apparatus of the present invention, the liquid containing the above ingredients is placed in a dispensing vessel capable of propelling a liquid in an aerosol, having a reservoir portion for holding the liquid, a nozzle means portion capable of being aligned to direct the aerosol towards the posterior pharyngeal region of a subject throat, and a label affixed to the reservoir potion of the vessel giving directions for use. The nozzle or delivery means may be a conventional inhaler tip or a pressured flow valve aperture.

BRIEF DESCRIPTION OF THE DRAWINGS

FIG. 1 is a side view in elevation of a first exemplary embodiment of a prior art container suitable for use with the present invention;

FIG. 2 is a side view in elevation of a second exemplary embodiment of a prior art container suitable for use with the present invention; and FIG. 3 is a side view in elevation of a third exemplary embodiment of a prior art container and dropper suitable for use with e present invention.

DETAILED DESCRIPTION OF THE PREFERRED EMBODIMENT

In the present invention, application of alveolar surfactant preparations to the posterior pharyngeal region in human subjects significantly reduces the sleep disturbance index (sum of hourly hypopneic and apnoeic episodes during sleep), and decreases the incidence of oxygen desaturation. The surfactant preparations may be any of those naturally occurring or artificially compounded compositions commercially available and licensed by the Food & Drug Administration for use in treating infant respiratory distress syndrome or its adult counterparts. Table 1 gives the tradename, source, manufacturer, and active ingredients of the principal commercial products. A preferred composition is Survanta (berectant), a modified natural bovine lung extract containing phospholipids, neutral lipids, fatty acids, surfactant-associated proteins including SP-B and SP-C, and supplemented with colfosceril palmitate (dipalmitoylphosphatidylcholine, DPPC), palmitic acid, and tripalmitin to mimic the surface-tension reducing properties of natural lung surfactant. The performance of these products in respiratory distress syndrome is evaluated in Merrit, et al., *Pediatric Pulmonology*, 14: 1 (1992).

TABLE 1

Surfactants

| Name | Source | Maker | Active components |
|---|---|---|---|
| Exosurf | artificial | Glaxo-Wellcome | phospholipid (DPPC) cetyl alcohol tyloxapol |
| Infasurf | calf lung | | phospholipid |
| Curosurf | porcine lung | Laboratoire Seron France | phospholipid |
| Survanta (berectant) | adult bovine lung | Ross Laboratories | phospholipids (DPPC, others) SP-B SP-C |
| KL4-surfactant | artificial | Johnson & Johnson | synthetic peptide phospholipid (DPPC, POPG) |

Lung surfactant may also be synthetically compounded of purified phospholipids, fatty acids, and apoproteins which through their highly hydrophobic properties, aid in anchoring the phospholipid ingredients to the mucosal surfaces of the pharynx. Various chemistries have been devised for effecting an ionic or even covalent association of these surfactant components. Canadian patent No. 2,042,635 (Sarin, et al.) discloses fatty acid/SP-C conjugates which may be used in conjunction with phospholipids and other surfactant ingredients. The conjugate has the advantage of providing the hydrophobic moiety which lowers and stabilizes surface tension values, and at the same time provides a polar solvent. Another synthetic surfactant composition useful in the practice of the present invention is disclosed in U.S. Pat. No. 4,826,821, and comprises dipalmitoyl phosphatidyl choline, a C-14 to C-18 fatty alcohol and a nonionic surface active agent, preferably tyloxapol.

Analysis of the phospholipid fraction of naturally occurring surfactant reveals a complex composition containing plasmenylcholine, phosphatidylcholine, choline glycerophospholipids, sphingomyelin, phosphatidylinositol, phosphatidylserine and lysophophatidylethanolamine, frequently appearing in difficult to separate pairs. See Dugan, et al., *J. Chromatography*, 378: 317 (1986) and U.S. Pat. No. 4,826,821, hereby incorporated by reference. The use of any of these phospholipids in purified form in low percentage amounts (about 0.5 to about 15 percent w/w) in combination with the major surfactant component, dipalmitoyl phosphatidyl choline (about 28 to 53 percent (w/w), and including or omitting SP-A, SP-B or SP-C is a synthetic form of surfactant applicable to the present invention. Preparation of the purified hydrophobic protein, as SP-C, may be carried out according to the procedures disclosed in WO87/06943, hereby incorporated by reference. Use of surfactant protein fragments is also efficacious, as the fragments exhibit unusual surface tension properties, as disclosed in U.S. Pat. No. 5,547,937 Sarin), and other patents in the related series. A pharmacologically effective dose of a hydrophillical apo protein SP-A and the hydrophobic apo protein SP-B, C is 0.25 to 2.5 percent of each and a total combined percentage of 4–6 percent. Any combination of the foregoing ingredients will have efficacy in the present invention so long as the tissue coating and adhesive properties of natural surfactant are mimicked, and most importantly, there is an effective lowering of surface tension of the film to values of 10 millinewtons or less (preferably from about 0.5 to 7 millinewtons).

The therapeutic use of these substances is in contrast to oil-based lubricants, which have some effect in reducing snoring, such as phosphocholinamin, the trade name for a mixture of lecithin complexed with a light hydrocarbon fraction, described in Hoffstein, et al., *Am. J. Otolarygol.*, 8:236 (1987). The present method is also in contrast to other human therapeutic approaches to reduce snoring specifically, such as the use of methysulfonylmethane in combination with a mild anesthetic, as taught in U.S. Pat. No. 5,569,679.

The surfactant solution is delivered in a convenient dose volume of about 0.5 to 1.5 ml. If a fine aerosol spray is used, the volume may be decreased to as little as 0.2 ml. Any amount will be effective so long as there is uniform continuous coating of the posterior pharyngeal surfaces. Volumes greater than about 1.5 ml are to be avoided as the excess will pool or drain off and be swallowed. The concentration of various ingredients generally simulates the natural surfactant, in that dipalmitoyl phosphatidyl choline is the predominant ingredient at 37 to 48 percent, in a preferred embodiment. A pharmacologically effective dose is an amount of surfactant containing 0.25 to 2.75 mg total ingredients dispersed in 0.75 to 1.5 ml solution. The composition is not diluted.

In one embodiment of the present invention, the surfactant composition is contained in a vessel adapted to deliver a surfactant aerosol to the posterior pharyngeal region. The vessel may be of three types: a pressurized aerosol can, a squeeze bottle, or a pump bottle. The surfactant will typically be applied through the oral cavity, but it may be delivered nasally when the subject is supine. Examples of containers suitable for nasal delivery are depicted in U.S. Pat. No. 5,569,679 incorporated by reference. For oral administration, a pump or squeeze bottle may be equipped with an elongated tapered nozzle (three to six inches in length) for local direct application of surfactant to the pharyngeal region. Conveniently, the spray bottle containing a pre-measured quantity of surfactant, to which appropriate label directions are affixed, may be distributed as an article of commerce. When packed under sterile conditions, the surfactant may be stored refrigerated or at room temperature.

With reference to FIGS. 1–3, it should be appreciated that the solution according to the present invention may be administered through a variety of known techniques, and the present invention is also directed to a product that may be used in treating snoring.

With reference to FIG. 1, a prior art container is shown which is of the type used to instill a metered quantity of solution. In FIG. 1, container 10 includes a bottle 12 for holding a solution of this invention. Applicator 14 includes a metering pump 16 activated by a plunger 18. Upon depressing plunger 18 toward bottle 12, a metered quantity of the solution in bottle 12 is ejected through the nozzle 20 which is placed in the nostril. When not in use, container 10 is enclosed by means cap 22 (shown in phantom). As noted, the container 10 is of a type known in the prior art for administering a selected metered quantity of the solution in bottle 12 is ejected through nozzle 20 which is placed in the nostril. When not in use, container 10 is of a type known to prior art for administering a selected metered dosage.

A second prior art container is shown in FIG. 2. Here, container 40 includes a plastic squeeze bottle 42 adapted to hold the fluid to be dispensed. Plastic squeeze bottle 42 communicates with a nozzle 44 that is threaded at 46 to receive a cap 48 (shown in phantom). Here, bottle 42 may be held upright with nozzle 44 positioned in the nostril. Upon squeezing, a mist of solution from bottle 42 is ejected through nozzle 44. Alternatively, bottle 42 may be inverted with nozzle 44 in the nostril and the solution administered dropwise.

In FIG. 3, a standard eye dropper-type container 60 is shown which includes a bottle 62 adapted to receive the fluid. Eye dropper 64 is received in bottle 62 and is threadably mounted thereto by cap 66 mounted on threaded neck 68. Eye dropper 64 includes a flexible bulb 70 which may be compressed to remove air therefrom. By immersing tip 72 of pipette portion 74 in fluid, the release of pressure on bulb 70 causes an amount of solution to be drawn into pipette 74. Pipette 74 may then be placed into the nostril and the solution administered in drop-wise manner.

Further advantages of the present invention will be apparent from the Example which follows.

EXAMPLE

Six individuals with varying degrees of sleep apnea were studied on two different nights at least 5 days apart under a research protocol approved by the University of Wisconsin Human Subjects Committee. These volunteer subjects were given saline (control) on one night and berectant (Survanta; natural bovine surfactant) on the other night. Once the subjects had fallen asleep as demonstrated by their EEG, they were monitored for 60 minutes without any intervention. One ml volumes of either saline or berectant were then delivered into the posterior pharynx via a small catheter (2.5 mm outer diameter and placed transnasally) after the subjects had fallen asleep as verified by electroencephalic (EEG) monitoring. For the 60 minutes prior to instillation of saline or berectant and the subsequent 60 minutes following instillation, sleep stage (I, II, III, IV, or REM) was monitored via EEG, inspiratory and expiratory air flow was monitored via a pneumotachometer attached to a close-fitting nasal mask, inspiratory muscle activity was monitored via electromyography with two surface electrodes placed 2 to 4 cm above the right costal margin in the anterior axillary line, arterial oxyhemoglobin saturation was continuously monitored via ear oximetry, and end-tidal $CO_2$ was measured breath to breath.

Hypopnea was defined as a 20% decrease in tidal volume in three or more consecutive breaths compared to the preceding breath, apnea as cessation of flow for $\geq 5$ seconds, and desaturation as $\geq 2\%$ decrease in oxygen saturation from baseline. A Respiratory Disturbance Index (RDI) was defined as the number of hypopneas, apneas, and desaturations per hour of sleep. The degree of desaturation for each event ($\Delta SpO_2\%$) was also computed. For a detailed discussion of sleep scoring techniques, see Mitler, et al., "Sleep Scoring Technique", in *Sleep Disturbances,* Yancy Press, NY: 1991.

The RDI for Stage II, III, and IV sleep combined, or for Stage II alone, significantly decreased following instillation of berectant but not following saline (Tables 2 and 3). Episodes of desaturation during Stage II, III, and IV sleep combined, or for Stage II sleep alone, also decreased (Tables 4 and 5). Additionally, the degree of desaturation for each event ($\Delta SpO_2\%$) diminished with berectant but not with saline, although this change did not reach statistical significance (p=0.09, Table 6).

Instillation of artificial surfactant into the upper airway of volunteer subjects with sleep-disordered breathing (sleep apnea/hypopnea) was associated with a modest but statistically significant reduction in RDI. Mucosal surface factors may modulate upper airway patency in patients with sleep apnea/hypopnea, and interventions to reduce mucosal surface tension may serve as an adjunctive therapy in many patients with sleep apnea/hypopnea syndromes.

TABLE 2

Respiratory Disturbance Index (Stage II, III, & IV sleep)

| Subject | Pre-saline | Post-saline | Pre-berectant | Post-berectant |
|---|---|---|---|---|
| 1 | 109.6 | 112.1 | 133.9 | 131.2 |
| 2 | 31.6 | 15.8 | 22.7 | 19.3 |
| 3 | 52.4 | 110.4 | 72.0 | 15.0 |
| 4 | 37.1 | 28.0 | 48.0 | 25.3 |
| 5 | 137.1 | 121.1 | 157.5 | 132.9 |
| 6 | 83.8 | 91.8 | 120.0 | 90.3 |
| Mean ± SEM | 75 ± 17 | 80 ± 19 | 92 ± 22 | 69 ± 23* |

*p < 0.05

TABLE 3

Respiratory Disturbance Index (Stage II sleep)

| Subject | Pre-saline | Post-saline | Pre-berectant | Post-berectant |
|---|---|---|---|---|
| 1 | 115.6 | 112.1 | 126.7 | 131.4 |
| 2 | 45.7 | 18.2 | 26.3 | 13.0 |
| 3 | 56.5 | 110.4 | 72.0 | 15.0 |
| 4 | 37.6 | 25.8 | 48.4 | 25.6 |
| 5 | 137.1 | 121.1 | 157.5 | 132.9 |
| 6 | 83.3 | 90.9 | 120.0 | 90.3 |
| Mean ± SEM | 79 ± 16 | 80 ± 19 | 92 ± 21 | 68 ± 23 |

TABLE 4

Desaturations (Stage II, III, & IV sleep)

| Subject | Pre-saline | Post-saline | Pre-berectant | Post-berectant |
|---|---|---|---|---|
| 1 | 106.1 | 105.8 | 126.2 | 125.6 |
| 2 | 17.4 | 7.4 | 17.7 | 12.4 |
| 3 | 8.7 | 4.8 | 4.0 | 5.0 |
| 4 | 12.0 | 17.9 | 5.5 | 8.0 |
| 5 | 131.4 | 105.6 | 132.5 | 45.7 |
| 6 | 49.3 | 71.1 | 81.6 | 67.1 |
| Mean ± SEM | 54 ± 22 | 52 ± 20 | 61 ± 24 | 44 ± 19 |

TABLE 5

| | | | Desaturations (Stage II sleep) | |
|---|---|---|---|---|
| Subject | Pre-saline | Post-saline | Pre-berectant | Post-berectant |
| 1 | 113.3 | 105.8 | 126.7 | 125.7 |
| 2 | 17.1 | 10.9 | 22.5 | 7.8 |
| 3 | 9.4 | 4.8 | 4.0 | 5.0 |
| 4 | 12.1 | 16.8 | 5.5 | 8.1 |
| 5 | 131.4 | 105.6 | 132.5 | 45.7 |
| 6 | 48.3 | 71.5 | 81.6 | 67.1 |
| Mean ± SEM | 55 ± 22 | 53 ± 19 | 62 ± 24 | 43 ± 19 |

TABLE 6

| | $\Delta SpO_2$, % | |
|---|---|---|
| Intervention | Pre | Post |
| Berectant | 3.7 ± 2.0 | 2.4 ± 1.5* |
| Saline | 3.5 ± 2.2 | 3.7 ± 1.5 |

What is claimed is:

1. A method for alleviating sleep hyponea and apnea episodes in a single pre-sleep treatment without disturbing the sleeper during a normal 7–9 hour period of rest comprising the single step of:
    applying a pulmonary alveolar surfactant preparation in a pharmacologically effective dose to the posterior pharyngeal region of a patient prior to said period of sleep whereby said periods of Sleep Hyponea and Apnea are alleviated for said 7–9 hour period.

2. A method according to claim 1 wherein the posterior pharyngeal region has a film thereon and the surfactant preparation lowers the surface tension of the film to less than about 10 millinewtons.

3. A method according to claim 1 wherein the surfactant preparation lowers the surface tension of the film to the range of about 0.5 to 7 millinewtons.

4. A method according to claim 1 wherein the pharmacologically effective dose is an amount of surfactant containing 0.25 to 2.75 mg total ingredients dispersed in 0.75 to about 1.5 ml of solution.

5. A method according to claim 1 wherein the surfactant preparation further includes a protein portion selected from the group consisting of SP-A, SP-B, SP-C, and SP-D in pharmacologically effective doses.

6. A method according to claim 1 wherein the phospholipid is selected from the group consisting of saturated phosphatidylcholine, unsaturated phosphatidylcholine, phosphatidylglycerol, dipalmitoylphosphatidylcholine, and combinations thereof.

7. A method according to claim 6 wherein the surfactant preparation includes a phospholipid.

8. A method according to claim 1 wherein the surfactant preparation further includes neutral lipids.

9. A method for treating sleep apnea by applying a surfactant preparation to the posterior pharyngeal region of a patient prior to a period of sleep, the posterior pharyngeal region having a film thereon, the method comprising the steps of:
    applying to the pharyngeal region a pharmacologically effective dose of a phospholipid-containing surfactant preparation, the surfactant preparation capable of lowering the surface tension of the film to less than about 10 millinewtons.

10. A method according to claim 9 wherein the surfactant preparation lowers the surface tension of the film to the range of about 0.5 to 7 millinewtons.

11. A method according to claim 9 wherein the pharmacologically effective does is an amount of surfactant containing 0.25 to 2.75 mg total ingredients dispersed in 0.75 to about 1.5 ml of solution.

12. A method according to claim 9 wherein the surfactant preparation further includes a protein portion selected from the group consisting of SP-A, SP-B, SP-C, and SP-D in pharmacologically effective doses.

13. A method according to claim 9 wherein the phospholipid is selected from the group consisting of saturated phosphatidylcholine, unsaturated phosphatidylcholine, phosphatidylglycerol, dipalmitoylphosphatidylcholine, and combinations thereof.

14. A method according to claim 9 wherein the surfactant preparation further includes neutral lipids.

* * * * *